US008063243B2

(12) United States Patent
Franckowiak et al.

(10) Patent No.: US 8,063,243 B2
(45) Date of Patent: Nov. 22, 2011

(54) STABLE ACTIVE COMPOUND COMPLEX OF SALTS OF O-ACETYLSALICYLIC ACID WITH BASIC AMINO ACIDS AND GLYCINE

(75) Inventors: Gerhard Franckowiak, Wuppertal (DE); Wolfram Ledwoch, Langenfeld (DE); Eberhard Schweinheim, Leverkusen (DE); Yutaka Hayauchi, Leverkusen (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 339 days.

(21) Appl. No.: 11/921,339

(22) PCT Filed: May 20, 2006

(86) PCT No.: PCT/EP2006/004799

§ 371 (c)(1), (2), (4) Date: Feb. 2, 2009

(87) PCT Pub. No.: WO2006/128600

PCT Pub. Date: Dec. 7, 2006

(65) Prior Publication Data

US 2009/0226524 A1 Sep. 10, 2009

(30) Foreign Application Priority Data

Jun. 2, 2005 (DE) ......................... 10 2005 025 283

(51) Int. Cl.
*C07C 65/10* (2006.01)

(52) U.S. Cl. ......................... 562/477; 424/489; 424/499

(58) Field of Classification Search ........................ None
See application file for complete search history.

(56) References Cited

U.S. PATENT DOCUMENTS

2002/0091108 A1 * 7/2002 Franckowiak et al. ....... 514/161

FOREIGN PATENT DOCUMENTS

| | | |
|---|---|---|
| EP | 0089198 | 9/1983 |
| GB | 2051573 | 1/1981 |
| JP | 56065816 | 6/1981 |
| RU | 2203064 | 4/2003 |
| WO | WO-02/05782 | 1/2002 |
| WO | WO-03/059323 | 7/2003 |
| WO | WO-2005/115404 | 12/2005 |

OTHER PUBLICATIONS

K. Nakai, et al. "Critical cerebral blood flow for production of hemiparesis after unilateral carotid occlusion in the gerbil," Journal of Neurology, Neurosurgery, and Psychiatry, 1977, pp. 595-599.
U. Gonullu et al: "Stability of aspirin-arginine and aspirin-lysine salts aspirin-." Acta Pharmaceutica Turcica, 1997, p. 39, Turkey.
Sudha R. Vippagunta et al., Advanced Drug Delivery Rev. 48, 2001, 3-26.

* cited by examiner

*Primary Examiner* — Sudhakar Katakam

(57) ABSTRACT

The present invention relates to stable active compound complexes of salts of o-acetylsalicylic acid with basic amino acids and glycine, to a process for their preparation and to their use as medicaments.

21 Claims, 2 Drawing Sheets

Figure 1:
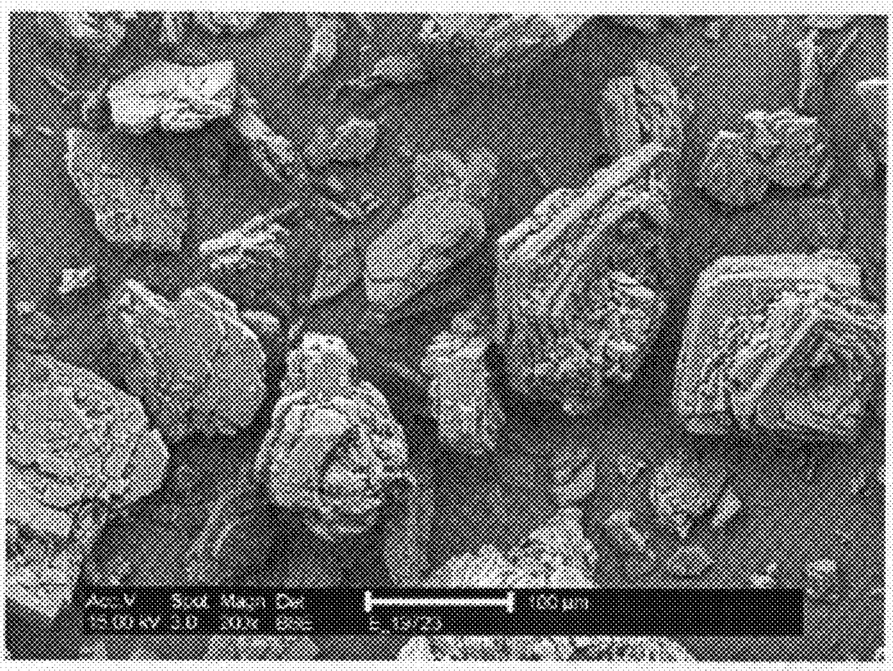

STABLE ACTIVE COMPOUND COMPLEX OF SALTS OF O-ACETYLSALICYLIC ACID WITH BASIC AMINO ACIDS AND GLYCINE

The present invention relates to stable active compound complexes of salts of o-acetylsalicylic acid with basic amino acids and glycine, to a process for their preparation and to their use as medicaments.

The analgesic action of o-acetylsalicylic acid (Aspirin®) has been utilized therapeutically for a long time. Thus, o-acetylsalicylic acid is used as an analgesic, antipyretic, antirheumatic, and also as a non-steroidal anti-inflammatory agent, for example for the treatment of arthritis, neuralgia and myalgia.

However, o-acetylsalicylic acid is only soluble to a limited extent, and the rate of bioabsorption is thus limited. In particular, in the case of pain, especially in the case of migraine, a rapid rise in the concentration of the active compound in the body is desirable and required for the therapeutic effect. Hitherto, this could only be achieved by suitable administration forms, such as, for example, buffered effervescent tablets or chewable tablets.

One option of quickly achieving high blood concentrations of the active compound is to increase the dissolution rate of the active compound itself. This can be achieved using salts of o-acetylsalicylic acid. Moreover, in the case of prolonged oral administration, it has to be emphasized that the o-acetylsalicylates are tolerated well.

Known salts of acetylsalicylic acid are, inter alia, salts of acetylsalicylic acid with basic amino acids. The basic amino acids used are in particular L-lysine, D,L-lysine or arginine. It is also possible to add a certain amount of glycine. Therapeutically, use is made of the salt of acetylsalicylic acid (ASS) with the amino acid lysine. The most frequently used medicament comprising ASS lysinate is an administration form for parenteral administration which additionally comprises glycine. It is commercially available under the name Aspisol® (until mid-2005). The glycine is added to the ASS lysinate in solid form, so that a mixture of ASS lysinate and glycine is present.

A certain disadvantage of the o-acetylsalicylates until now was their inadequate stability. On the one hand, a restricted shelf-life of the pharmaceutical preparations produced from these salts results from this. On the other hand, sterilization of the active compound, which may be necessary, cannot be carried out by means of heat sterilization because of the inadequate thermal stability of these salts, but must be carried out in other ways, for example, by introduction of ethylene oxide gas.

The low stability of the o-acetylsalicylates is to be attributed to a back reaction of the product to o-acetylsalicylic acid and the corresponding amino acid known to the person skilled in the art. The amino acid then reacts with the o-acetylsalicylic acid with removal of the acetyl group (amidolysis) and release of salicylic acid. The presence of free salicylic acid in pharmaceutical preparations, however, is undesirable and therefore to be restricted to a low, acceptable value (Arch. Pharm. 318, 120, 1985).

WO 02/005782 and WO 03/059323 describes salts of o-acetylsalicylic acid with basic amino acids, which salts have increased stability and therefore do not have the disadvantages of the o-acetylsalicylates known to date with respect to storage and/or sterilizability. The salts are prepared by a special process and, when the particle size distribution is measured using a Malvern 2600D apparatus under standard conditions, have a mean particle size above a particle size of 160 μm, a proportion of more than 60% of the particles having a particle size in a range from 100 to 200 μm. They may comprise a certain amount of added glycine. Furthermore, WO 02/005782 and WO 03/059323 describe that addition of glycine is not required and that this type of addition has no effect on the properties of the o-acetylsalicylate; in particular, the presence of glycine has no effect on the stability of the o-acetylsalicylates.

Surprisingly, it has now been found that the way in which the glycine is added during the production of the o-acetylsalicylate has a considerable effect on the properties of the o-acetylsalicylate.

The present invention relates to active compound complexes of salts of o-acetylsalicylic acid with basic amino acids and glycine.

The active compound complex according to the invention is distinguished by high stability and has a characteristic crystal form. This is illustrated in more detail by the attached pictures:

FIG. 1: Electron-microscopic photo of the crystals of Aspisol (commercial product until mid-2005).

Figure 2:
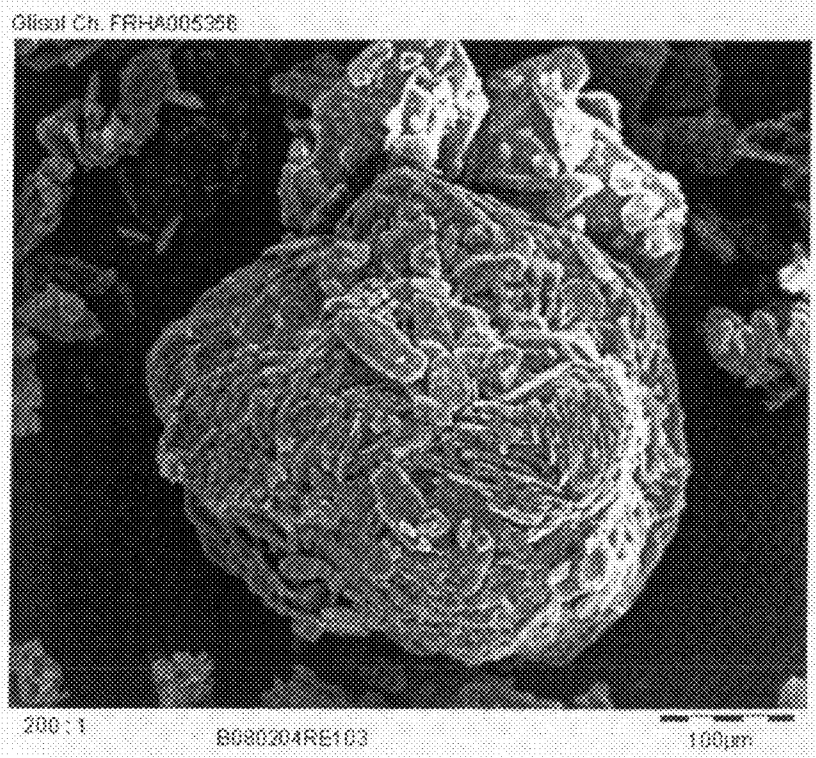

FIG. 2: Electron-microscopic photo of a crystal of the active compound complex according to the invention of D,L-lysinate of o-acetylsalicylic acid with glycine according to Example 1.

Figure 3:
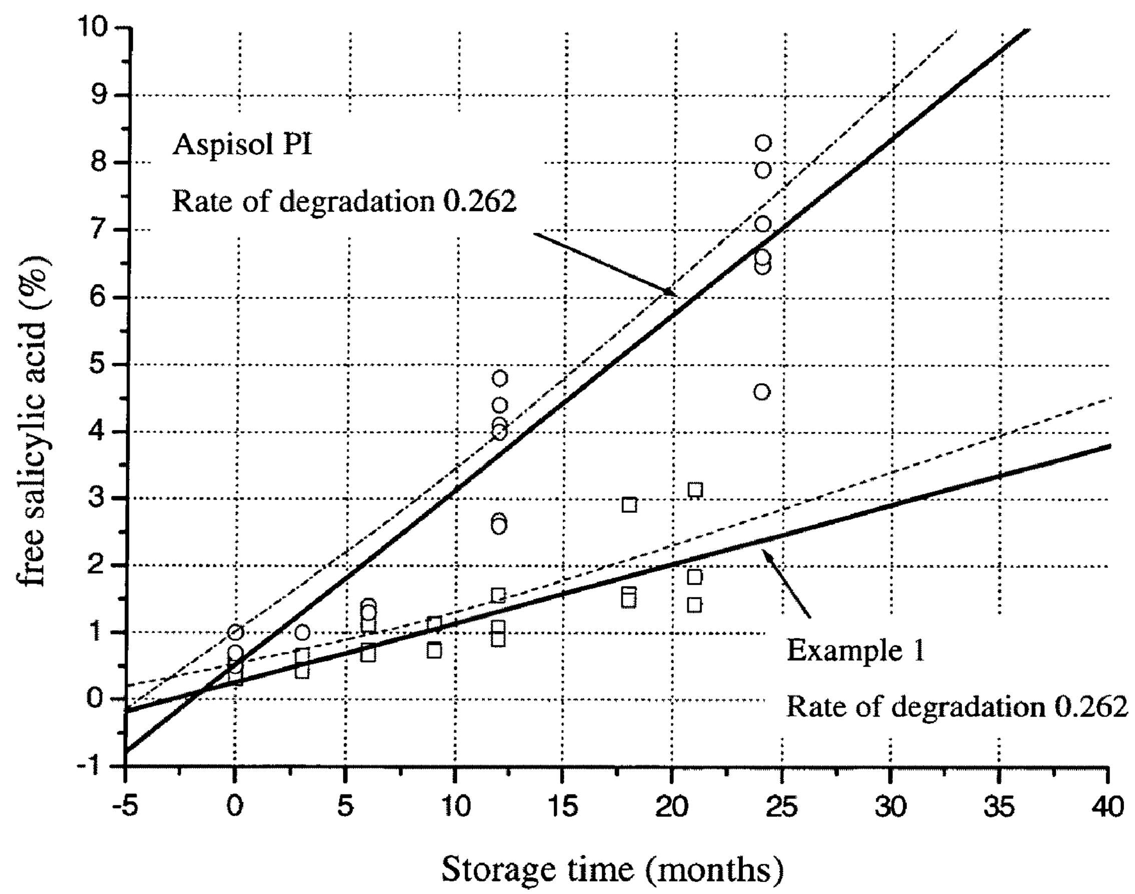

FIG. 3: Stability data of Aspisol (commercial product until mid-2005) and Example 1, storage conditions: 25° C./60% relative atmospheric humidity—what is measured is the formation of salicylic acid.

FIG. 1 shows crystals of Aspisol (commercial product until mid-2005), in which the D,L-lysinate of o-acetylsalicylic acid and glycine are present side-by-side as a mixture. This is due to the preparation process in which the glycine and the D,L-lysinate of o-acetylsalicylic acid are, towards the end, mixed with one another as dry solid substances. In contrast, FIG. 2 reflects the clearly different crystal form of the Example 1 according to the invention.

FIG. 3 shows the considerably improved stability of Example 1 compared to Aspisol (commercial product until mid-2005). After 30 months, for example, one third less of salicylic acid is released.

The basic amino acids suitable according to the invention for forming the o-acetylsalicylates can be present in the L- or the D-configuration or else as a mixture of D- and L-form. According to the invention, the term "amino acids" refers in particular to the naturally occurring L-amino acids, but also includes solvates, such as, for example, hydrates, homologues, isomers and derivatives thereof. An example of isomers that may be mentioned are enantiomers. Derivates may, for example, be amino acids provided with protective groups. Typical examples of basic amino acids which may be mentioned are: lysine, arginine, ornithine, diaminobutyric acid. The salt of o-acetylsalicylic acid with lysine may be mentioned as being preferred.

The term according to the invention "active compound complex" describes a product consisting of crystals of a salt of o-acetylsalicylic acid with a basic amino acid and glycine, which crystals are intergrown closely. A crystal mixture of the individual components o-acetylsalicylate and glycine is not present.

The glycine content in the crystals according to the invention is from 8 to 12, preferably from 9 to 11, particularly preferably 10 per cent by weight, based on the active compound complex.

The advantageous properties of the present invention are observed independently of the particle size of the active compound complex according to the invention. Thus, the particle size distribution of the active compound complex according to the invention may, for example, have a mean particle size of preferably less than 100 μm, particularly preferably less than 70 μm.

Preparation:

According to the present invention, solutions of the reactants, i.e. of o-acetylsalicylic acid and the appropriate amino acid, are combined as quickly as possible under atmospheric pressure, preferably in less than 20 minutes, at a temperature of less than or equal to 40° C., preferably of from 20 to 35° C., and mixed to give a homogeneous phase, in a manner such that the temperature does not exceed 40° C. If required, seed crystals are added to the homogeneous mixture prepared in this manner and the mixture is cooled to from −5 to 10° C., preferably from 0 to 5° C., and the solution is stirred at this temperature for 2 to 8 hours, preferably for 3 to 5 hours. Cooled acetone and the required amount of glycine, which is cooled, if required, are added. To bring the crystallization to completion, the suspension should be kept under the conditions given above for at least 1 hour. Preferred according to the invention is a crystallization time of from 1 to 10 hours under the conditions mentioned above, a period of from 1 to 8 hours being particularly preferred. In accordance with the present invention, it is very important to keep the temperature during the crystallization process within relatively narrow limits. The temperature must not exceed 5° C. and should preferably be kept below 3° C., particularly preferably between 0 and 2° C. The seed crystals used can be crystals of the desired product. The crystallization is preferably carried out under atmospheric pressure.

The crystals are then isolated in a customary manner, for example by filtration or centrifugation. The solid is washed repeatedly with organic solvents, where, in accordance with the invention, preference is given to alcohols such as, for example, ethanol and/or ketones such as acetone or mixtures of alcohols and/or ketones, for example mixtures of ethanol and acetone, or the use of different such solvents.

The solid is then dried under reduced pressure. Here, the temperature should be kept below 50° C., preferably below 40° C. and particularly preferably below 35° C. A pressure of less than 100 mbar, preferably less than 50 mbar, should be applied to the solid. The drying can be carried out under customary conditions, for example, in a drying apparatus.

Suitable solvents for the reactants are water and water-miscible organic solvents such as, for example, alcohols, such as methanol, ethanol or isopropanol, in particular ethanol, ethers such as tetrahydrofuran (THF) or ketones such as acetone, or mixtures of the solvents mentioned. Preference is given to water, ethanol or a mixture of both.

The o-acetylsalicylic acid is preferably dissolved in ethanol and the amino acid, preferably lysine, particularly preferably D,L-lysine monohydrate, is added dissolved in water.

The reactants are employed in amounts such that a slight excess of the basic amino acid is present, based on the mol of o-acetylsalicylic acid. Preferred, according to the invention, is a molar ratio of o-acetylsalicylic acid to amino acid of from 1:1.05 to 1:1.5, a ratio of o-acetylsalicylic acid to amino acid of from 1:1.05 to 1:1.2 being particularly preferred.

In accordance with the present invention, the o-acetylsalicylic acid solution should have an o-acetylsalicylic acid content of from 1 to 10% by weight, preferably from 5 to 10% by weight and particularly preferably from 6 to 8% by weight. The solution of the basic amino acid should have an amino acid content of from 10 to 40% by weight, preferably from 15 to 35% by weight and particularly preferably from 20 to 30% by weight.

In accordance with the present invention, the glycine can be added to the reaction mixture of the reactants as a solution in water or a water-miscible organic solvent, where the solvents described above are suitable for use as organic solvents.

However, in accordance with the present invention, the glycine can also be added in the form of a suspension. The glycine suspension can be prepared in a customary manner. Preference according to the invention is given to preparing a glycine suspension from a solvent mixture of water and an alcohol, such as, for example, ethanol.

In the process according to the invention, it is also important that a certain stirring energy is maintained during crystallization. Stirring of the homogeneous mixture of the starting materials must be gentle. The stirring energy to be applied should not exceed 0.1 W per liter of reaction medium. According to the invention, preference is given to an applied stirring energy of from 0.04 to 0.06 W per liter of reaction medium. Suitable stirrers are all conventional stirring apparatus which can be regulated in an appropriate manner, such as, for example, a mixing vessel with flow spoiler.

It is also possible to carry out the entire process according to the invention under sterile conditions. The modifications required for this purpose of the above procedure, for example, with respect to sterilization of the starting materials and the apparatus used, are familiar to the person skilled in the art.

Medicaments:

The present invention also includes pharmaceutical preparations which, in addition to non-toxic inert pharmaceutically acceptable auxiliaries comprise the active compound complex according to the invention, and processes for producing these preparations.

The active compound complex can act systemically and/or locally. For this purpose, it may be administered in a suitable manner, such as, for example, orally or parenterally. For these administration routes, the active compound complex may be administered in suitable administration forms.

For oral administration, known administration forms for releasing the active compound complex rapidly and/or in modified form are suitable, such as tablets (uncoated and coated tablets, for example enteric coatings, FDT (fast-dissolve tablets), effervescent tablets, chewable tablets), capsules, coated tablets, granules, pellets, powders, emulsions, suspensions and solutions.

Parenteral administration can be carried out with circumvention of a bioabsorption step (intravenous, intra-arterial, intracardial, intraspinal or intralumbar) or including a bioabsorption (intramuscular, subcutaneous, intracutaneous or intraperitoneal). Administration forms suitable for parenteral administration are, inter alia, preparations for injection and infusion in the form of solutions, suspensions or emulsions.

Preferred is an administration as a preparation for injection and infusion. These may be finished preparations for injection or infusion in the form of solutions, suspensions or emulsions or else administration forms in which the active compound complex is present, for example, as a lyophilisate or sterile powder, separately from the solvent for injection or infusion, and the finished preparation for injection or infusion can be prepared only shortly before the administration by mixing with the solvent, for example, water.

Topical application in the form of suppositories or transdermal systems (for example patches, ETS systems) and also in creams, ointments, gels, sprays or dissolved in organic or inorganic solvents are further administration possibilities.

The active compound complex according to the invention can be converted in a manner known per se into the administration forms mentioned. This is carried out using inert non-toxic pharmaceutically suitable auxiliaries. These include, inter alia, carriers (for example microcrystalline cellulose), solvents (for example liquid polyethylene glycol), emulsifiers (for example sodium dodecylsulphate), dispersants (for example polyvinylpyrrolidone), synthetic and natural biopolymers (for example albumin), stabilizers (for example antioxidants such as ascorbic acid), colorants (for example inorganic pigments such as iron oxides) or taste and/or odour corrigents.

In general, it has proved advantageous both in human and in veterinary medicine to administer the active compound complex according to the invention in total amounts of from about 0.5 to about 500, preferably from 5 to 100 mg/kg of body weight every 24 hours, if appropriate in the form of several individual doses, to achieve the desired results. An individual dose contains the active compound complex according to the invention preferably in amounts from about 1 to about 80, in particular from 3 to 30 mg/kg of body weight.

Use:

The medicaments according to the invention can be employed as an analgesic, antipyretic, antirheumatic, and also as non-steroidal anti-inflammatory agents, for example for the treatment of diseases of the rheumatic type, arthritic disorders, neuralgia, myalgia and/or migraine. In particular, however, they can also be employed as platelet aggregation inhibitors in the prevention and therapy of cardiovascular and cerebrovascular diseases, for example in ischemic heart diseases, stroke, stable and unstable angina pectoris, myocardial infarction (for example, acute myocardial infarction), by-pass operations, PTCA (percutaneous transluminal coronary angioplasty) and/or stent implantation. Further application areas are stimulation of the immune system in HIV patients and tumour prophylaxis (for example carcinoma of the colon, oesophagus or lung), slowing of the cognitive deterioration in dementia syndrome (for example Alzheimer's disease), intermission of gallstone formation and the treatment of diabetic diseases.

Furthermore, the active compound complex according to the invention exhibits anti-asthmatic activity when inhaled.

WORKING EXAMPLES

Example 1

D,L-Lysine Acetylsalicylate with 10% Glycine

Through a sterile filter, a pyrogen-free solution of 40.0 kg of o-acetylsalicylic acid in 500 kg of ethanol is added to a sterile and pyrogen-free mixing vessel with flow spoiler. At 20 to 30° C. within a short period of time (less than 15 minutes) a sterile-filtered and pyrogen-free solution of 36.4 kg of D,L-lysine monohydrate in 110 kg of pyrogen-free water is added with stirring and cooling such that a temperature of 35° C. is not exceeded. At least 20 g of sterile seed crystals are added, and the mixture, which is already crystallizing, is, with reduced stirrer speed, cooled to 2° C. 490 kg of pyrogen-free and temperature-adjusted acetone and an aseptic and temperature-adjusted prepared suspension of 8.0 kg of glycine in 25.0 kg of pyrogen-free water and 90 kg of ethanol are then added. With further cooling at 2° C. the suspension is stirred for another 1 to 8 hours. Only then is the crystaline mixture isolated under aseptic conditions on a filter or in a centrifuge. On the separation apparatus the moist product is washed with pyrogen-free ethanol and acetone and dried under aseptic conditions up to a pressure of ≦50 mbar and a temperature of not more than 40° C. The finished product is then filled into vessels with PE inliners and sealed. What is obtained is 60 to 70 kg (75 to 87% of theory) of the title product having a residual moisture of <0.3% and a mean particle size of 41 μm.

Melting Point Determinations by DSC (Differential Scanning Calorimetry):

The melting point determinations are carried out by DSC using the Pyris-1 instrument from PerkinElmer with a heating rate of 20 K/min. The protective gas used is dry nitrogen. The characteristic DSC curves of Aspisol® (commercial product until mid-2005) and the product according to Example 1 show two peaks, an endothermic peak followed by an exothermic peak. The endothermic peak is due to the melting process, whereas the exothermic peak results from an overlap of disintegration and partial crystallization of a disintegration product (for example, acetylsalicylic acid) in the molten phase.

TABLE 1

| Batch | Peak temperature [° C.] (endothermic) | Peak temperature [° C.] (exothermic) |
|---|---|---|
| Aspisol ® (commercial product until mid-2005) | 144.4 ± 2.48 | 149.0 ± 2.0 |
| Example 1 | 147.9 ± 1.44 | 153.0 ± 1.0 |

The invention claimed is:

1. An active compound complex consisting essentially of a salt of o-acetylsalicylic acid with a basic amino acid and glycine, wherein said active compound complex comprises about 10 percent by weight of glycine and the melting range of the active compound complex has an endothermal peak temperature of 148±2° C. and an exothermal peak temperature of 153±2° C., and wherein said active compound complex has a particle size distribution having a mean particle size of less than 100 μm.

2. The active compound complex according to claim 1 with lysine as the basic amino acid.

3. The active compound complex according to claim 1 with D,L-lysine as the basic amino acid.

4. A process for preparing an active compound complex as defined in claim 1, comprising rapidly combining o-acetylsalicylic acid and a basic amino acid by stirring in water or a water-miscible organic solvent at a temperature of less than or equal to 40° C. to form a homogeneous mixture, cooling the homogeneous mixture to a temperature of from −5 to 10° C., adding acetone and glycine, continuing stirring for at least 1 hour to facilitate crystal formation, isolating the crystals and, during crystallization, maintaining a temperature of less than or equal to 5° C.

5. The process according to claim 4, wherein the basic amino acid used is D,L-lysine monohydrate.

6. The process according to claim 4, wherein the glycine is employed as a suspension.

7. The process according to claim 4, wherein, prior to the addition of acetone, seed crystals are added.

8. The process according to claim 7, wherein, after the addition of the seed crystals, the mixture is stirred at from 0 to 5° C. for 2 to 8 hours.

9. The process according to claim 4, wherein the ratio of the molar equivalents of o-acetylsalicylic acid to amino acid in the reaction solution is from 1:1.05 to 1:1.2.

10. The process according to claim 4, wherein during crystallization the stirring energy is not more than 0.1 W per liter of reaction medium.

11. The process according to claim 4, wherein the process is carried out under sterile conditions.

12. An active compound complex obtainable by a process according to claim 4.

13. A medicament comprising at least one active compound complex according to claim 1 or 12.

14. The medicament according to claim 13, wherein it is in a parenteral administration form.

15. The medicament according to claim 13, wherein it is a preparation for injection and infusion in the form of a solution, suspension or emulsion.

16. The medicament according to claim 13, wherein it is in an application form in which the active compound complex is present, separately from the solvent for injection or infusion, and the finished preparation for injection or infusion is prepared only shortly before the administration by mixing with the solvent.

17. The medicament according to claim 16 wherein water is employed as solvent for injection or infusion.

18. The medicament according to claim 13 for the intravenous, intra-arterial, intracardial, intraspinal, intralumbar, intramuscular, subcutaneous, intracutaneous or intraperitoneal administration.

19. A method for the treatment of arthritis, neuralgia, myalgia, and/or migraine, comprising administering an effective amount of an active compound complex according to claim 1.

20. A method for the treatment of myocardial infarction, stroke, ischemic heart diseases, angina pectoris, bypass operations, PTCA and/or stent implantation, comprising administering an effective amount of an active compound complex according to claim 1.

21. The medicament according to claim 16, wherein the active compound complex is present as a lyophilisate or sterile powder.

* * * * *